(12) United States Patent
Kishi

(10) Patent No.: US 10,983,331 B2
(45) Date of Patent: Apr. 20, 2021

(54) ENDOSCOPE AND IMAGE PICKUP UNIT

(71) Applicant: OLYMPUS CORPORATION, Tokyo (JP)

(72) Inventor: Tatsuya Kishi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/738,293

(22) Filed: Jan. 9, 2020

(65) Prior Publication Data

US 2020/0201023 A1     Jun. 25, 2020

Related U.S. Application Data

(63) Continuation of application No. PCT/JP2018/018315, filed on May 11, 2018.

(30) Foreign Application Priority Data

Jul. 12, 2017  (JP) .............................. JP2017-136418

(51) Int. Cl.
```
G02B 23/24      (2006.01)
H04N 5/225      (2006.01)
G03B 9/02       (2021.01)
A61B 1/00       (2006.01)
```

(52) U.S. Cl.
CPC ........... *G02B 23/2438* (2013.01); *G03B 9/02* (2013.01); *H04N 5/2254* (2013.01); *A61B 1/00009* (2013.01); *H04N 2005/2255* (2013.01)

(58) Field of Classification Search
CPC .......... H04N 7/18; H04N 9/47; H04N 5/2254; H04N 2005/2255; G02B 23/2438; G03B 9/02; A61B 1/00009

USPC ................................................ 348/65, 71, 76
See application file for complete search history.

(56) References Cited

U.S. PATENT DOCUMENTS

| | | | | |
|---|---|---|---|---|
| 5,817,014 A | * | 10/1998 | Hori ................... | A61B 1/00096 600/118 |
| 8,394,013 B2 | * | 3/2013 | Ichimura .............. | A61B 1/0623 600/129 |
| 2007/0149855 A1 | * | 6/2007 | Noguchi ............ | A61B 1/00188 600/168 |
| 2011/0205651 A1 | | 8/2011 | Yamano et al. | |

FOREIGN PATENT DOCUMENTS

| | | |
|---|---|---|
| EP | 2 454 985 A1 | 5/2012 |
| JP | 2000-037343 A | 2/2000 |
| JP | 2005-070366 A | 3/2005 |
| JP | 2007-313364 A | 12/2007 |
| JP | 2010-102265 A | 5/2010 |
| WO | 2011/007435 A1 | 1/2011 |
| WO | 2015/083490 A1 | 6/2015 |

OTHER PUBLICATIONS

International Search Report dated Jul. 31, 2018 received in PCT/JP2018/018315.

* cited by examiner

*Primary Examiner* — Trang U Tran
(74) *Attorney, Agent, or Firm* — Scully, Scott, Murphy & Presser, P.C.

(57) ABSTRACT

An image pickup unit includes a brightness aperture configured to determine a brightness of an observation optical system and a light shielding aperture, and the light shielding aperture is configured to block some of predetermined light fluxes that pass through the brightness aperture when a movable lens frame moves toward a telephoto side.

21 Claims, 16 Drawing Sheets

ENDOSCOPE AND IMAGE PICKUP UNIT

CROSS REFERENCE TO RELATED APPLICATION

This application is a continuation application of PCT/JP2018/018315 filed on May 11, 2018 and claims benefit of Japanese Application No. 2017-136418 filed in Japan on Jul. 12, 2017, the entire contents of which are incorporated herein by this reference.

BACKGROUND OF THE INVENTION

1. Field of the Invention

The present invention relates to an endoscope and an image pickup unit in which a movable lens configured to be movable in an optical axis direction is provided in an optical system.

2. Description of the Related Art

As is well known, an endoscope has been widely used for observation, treatment, or the like within a living body (within a body cavity) or inspection, repair, or the like within an industrial plant facility. In recent years, as an image pickup unit provided in a distal end section in this type of endoscope, an image pickup unit including an observation optical system unit configured to change a focal length by moving an observation optical system in a shooting optical axis direction and implement a zooming function for performing focus adjustment of a picked-up image or adjustment of a magnification on a wide/telephoto side or the like has been proposed and put to practical use.

As such an observation optical system unit, Japanese Patent Application Laid-Open Publication No. 2000-37343 discloses an objective optical system unit (observation optical system unit) including a front group lens frame, a front group lens including a plurality of optical members held on a distal end side of the front group lens frame, a rear group lens frame fitted in an extension portion on a proximal end side of the front group lens frame, a rear group lens including a plurality of optical members held in the rear group lens frame, a movable lens frame arranged movably in an optical axis direction in a gap portion provided between the front group lens frame and the rear group lens frame, and a focus adjustment lens mounted on the movable lens frame. Note that in the objective optical system unit, the front group lens frame is provided with a brightness aperture configured to cut a part of incident light, and each of the front group lens frame and the movable lens frame is further provided with a flare aperture for cutting stray light.

In this type of image pickup unit, a higher magnification on the telephoto side has been advanced. In the endoscope including the image pickup unit, observation is performed by arranging the distal end section approximately 30 mm to 50 mm away from a subject when a movable lens is on the wide side while being performed by arranging the distal end section at a position as significantly close as approximately 1 mm to 2 mm to the subject when the movable lens is on the telephoto side.

SUMMARY OF THE INVENTION

According to an aspect of the present invention, there is provided an endoscope including an optical system including a fixed lens and a movable lens and configured to be able to switch a focal position to a subject at a first distance and a subject at a second distance closer than the first distance, a fixed frame configured to hold the fixed lens, a moving frame configured to hold the movable lens and to be movable toward a side corresponding to the first distance and a side corresponding to the second distance along a direction of an optical axis of the optical system, a brightness aperture configured to determine a brightness of the optical system, an image pickup device configured to generate a video signal from an object image formed by the optical system, an illumination unit configured to illuminate a subject, and a light shielding aperture configured to block some of predetermined light fluxes that can pass through the brightness aperture when the moving frame moves from the side corresponding to the first distance to the side corresponding to the second distance.

According to another aspect of the present invention, there is provided an endoscope including an illumination optical system configured to irradiate an object with light, an observation optical system including a fixed lens and a movable lens and configured to be able to switch a focal position to a first distance and a second distance closer than the first distance, a fixed frame configured to hold the fixed lens, a moving frame configured to hold the movable lens and to be able to switch the focal position to the first distance and the second distance by moving to advance and retreat along a direction of an optical axis of the optical system, an image pickup device configured to generate a video signal from an object image formed by the observation optical system, a brightness aperture configured to restrict incident light and determine a brightness of the observation optical system, and a light shielding aperture configured to restrict incident light and to change a light amount restricted depending on whether a focal length is the first distance or the second distance, in which in the light shielding aperture, a distance from an edge forming an opening section configured to pass light to the optical axis is longer in a direction in which the illumination optical system is not arranged than in a direction in which the illumination optical system is arranged using the optical axis as a reference.

According to still another aspect of the present invention, there is provided an image pickup unit including an optical system including a fixed lens and a movable lens and configured to be able to switch a focal position to a subject at a first distance and a subject at a second distance closer than the first distance, a fixed frame configured to hold the fixed lens, a moving frame configured to hold the movable lens and to be movable toward a side corresponding to the first distance and a side corresponding to the second distance along a direction of an optical axis of the optical system, a brightness aperture configured to determine a brightness of the optical system, an image pickup device configured to generate a video signal from an object image formed by the optical system, and a light shielding aperture configured to block some of predetermined light fluxes that can pass through the brightness aperture when the moving frame moves from the side corresponding to the first distance to the side corresponding to the second distance.

DETAILED DESCRIPTION OF THE PREFERRED EMBODIMENT

Figure 2:
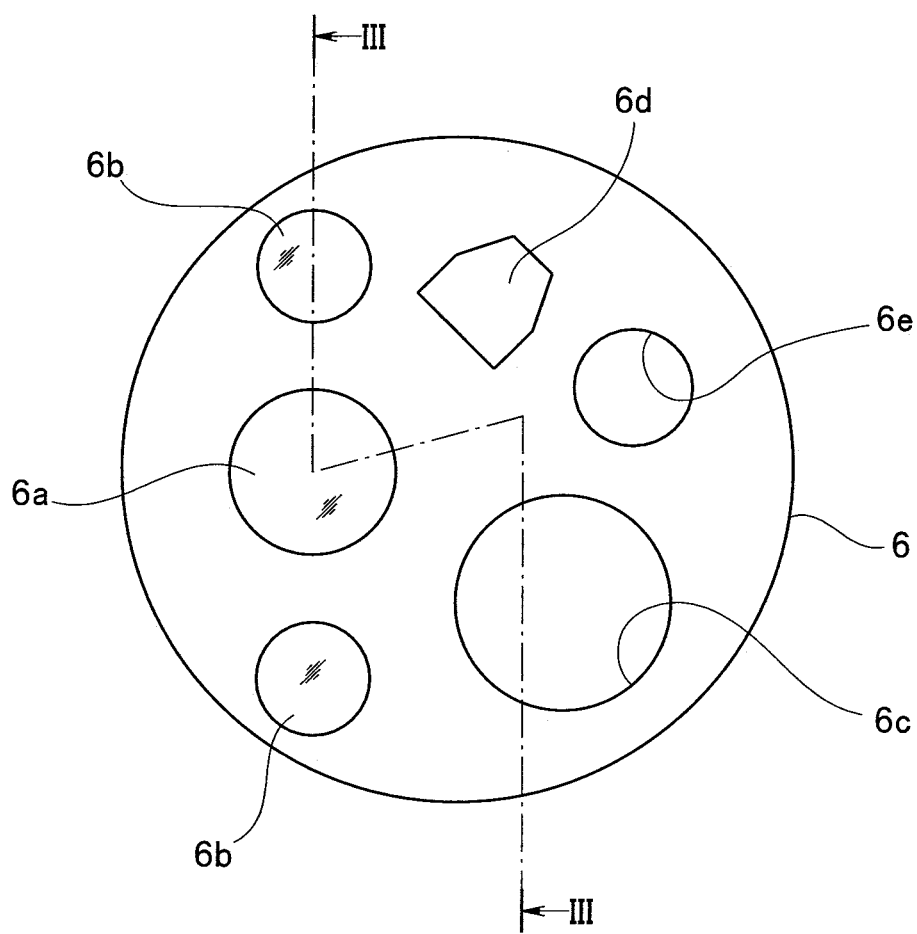
FIG. 2 is an end view of a distal end section.
Figure 3:
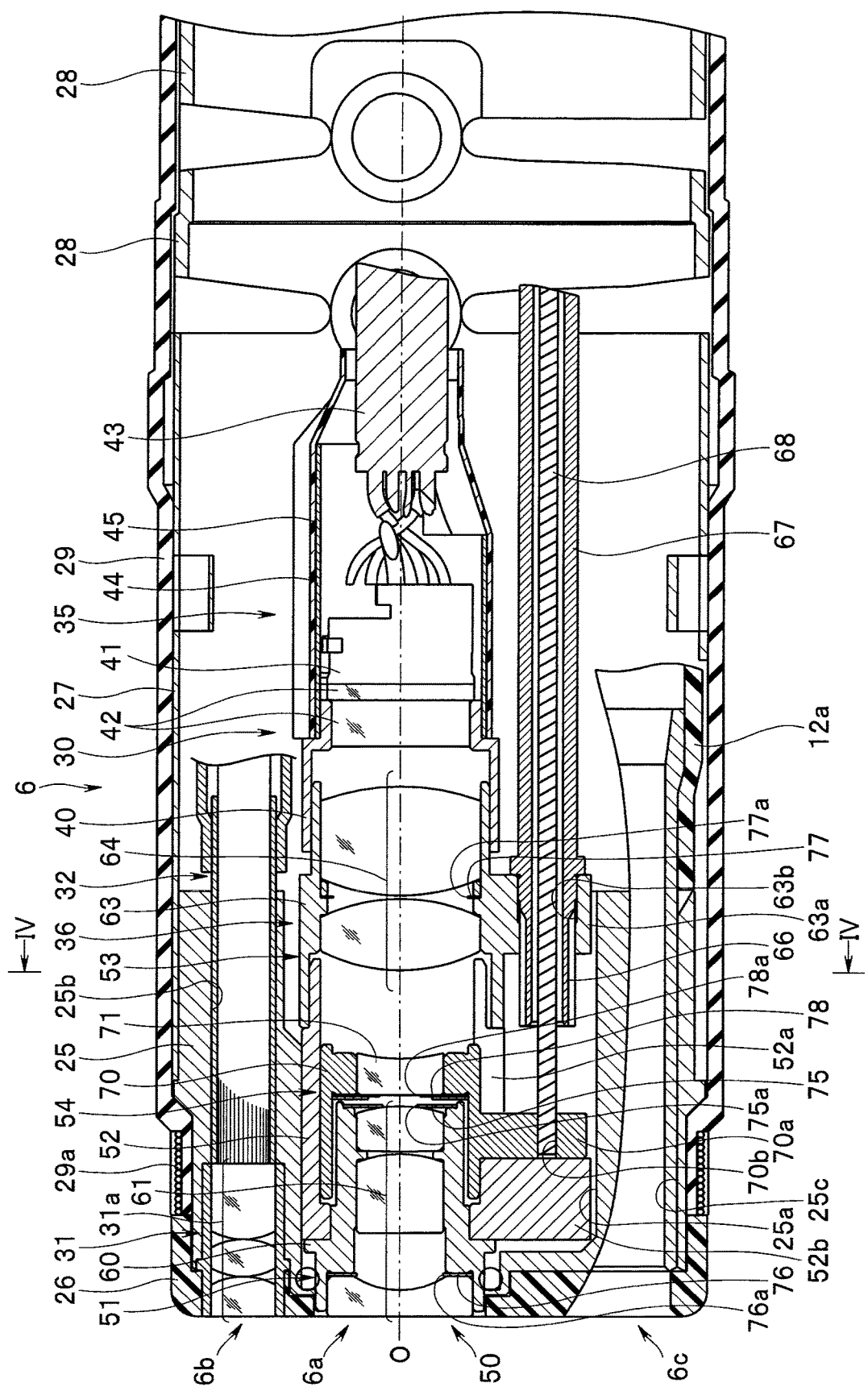
FIG. 3 is a cross-sectional view illustrating a distal end rigid member along a line III-III illustrated in FIG. 2.
Figure 4:
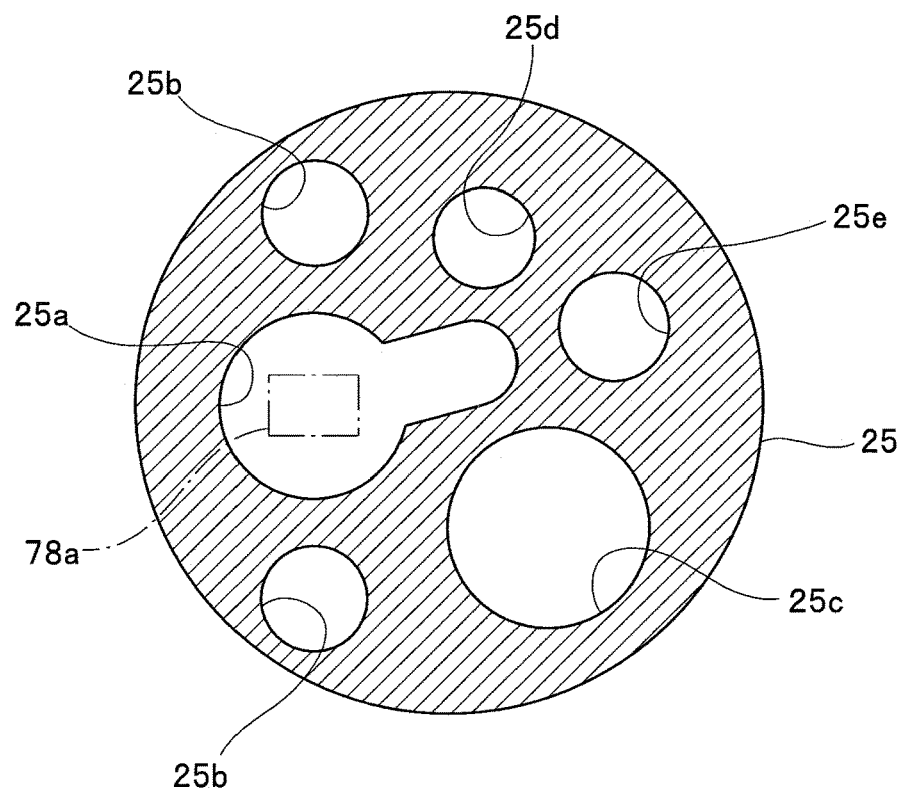
FIG. 4 is a cross-sectional view taken along a line IV-IV illustrated in FIG. 3.
Figure 5:
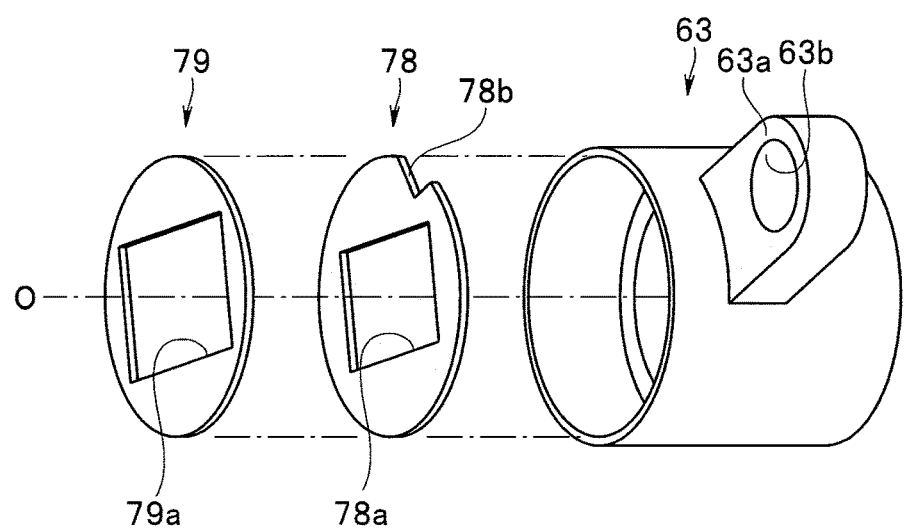
FIG. 5 is an exploded perspective view illustrating a movable lens frame, a brightness aperture, and a light shielding mask.
Figure 6:
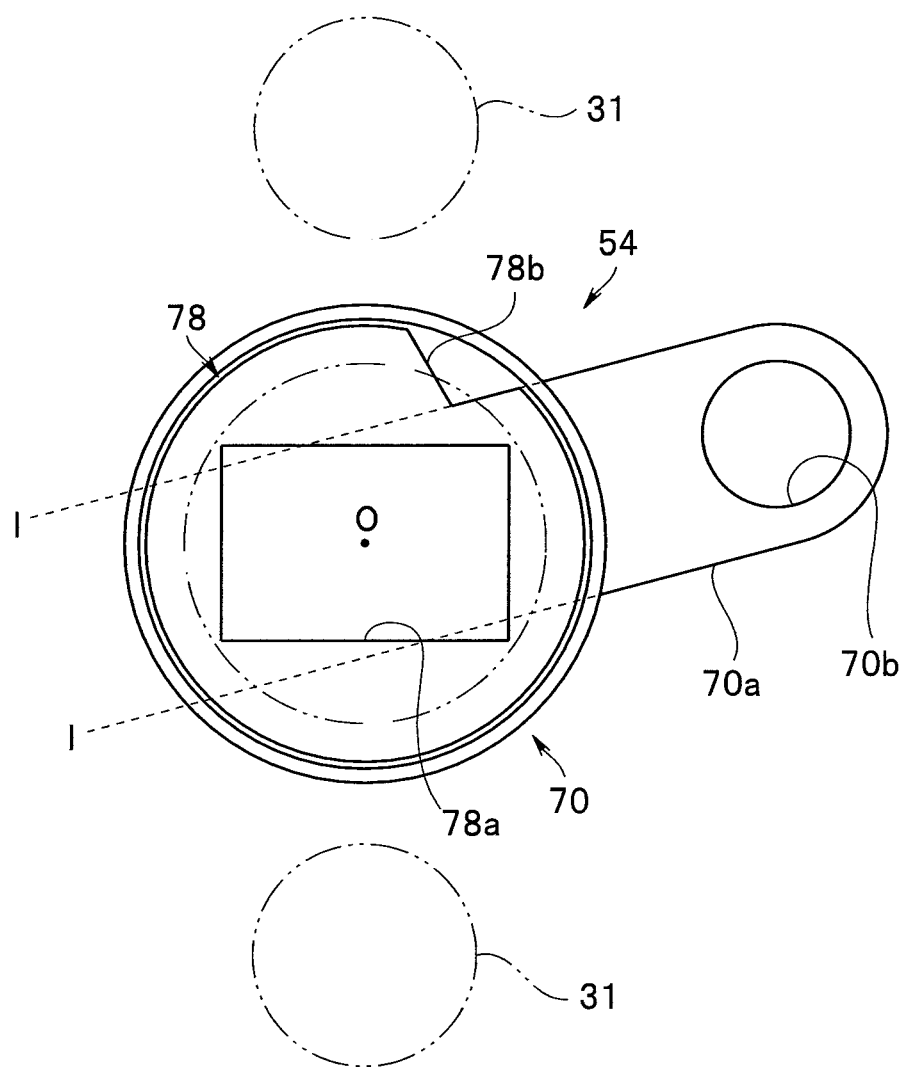
FIG. 6 is a plan view of the brightness aperture disposed in the movable lens frame.
Figure 7:
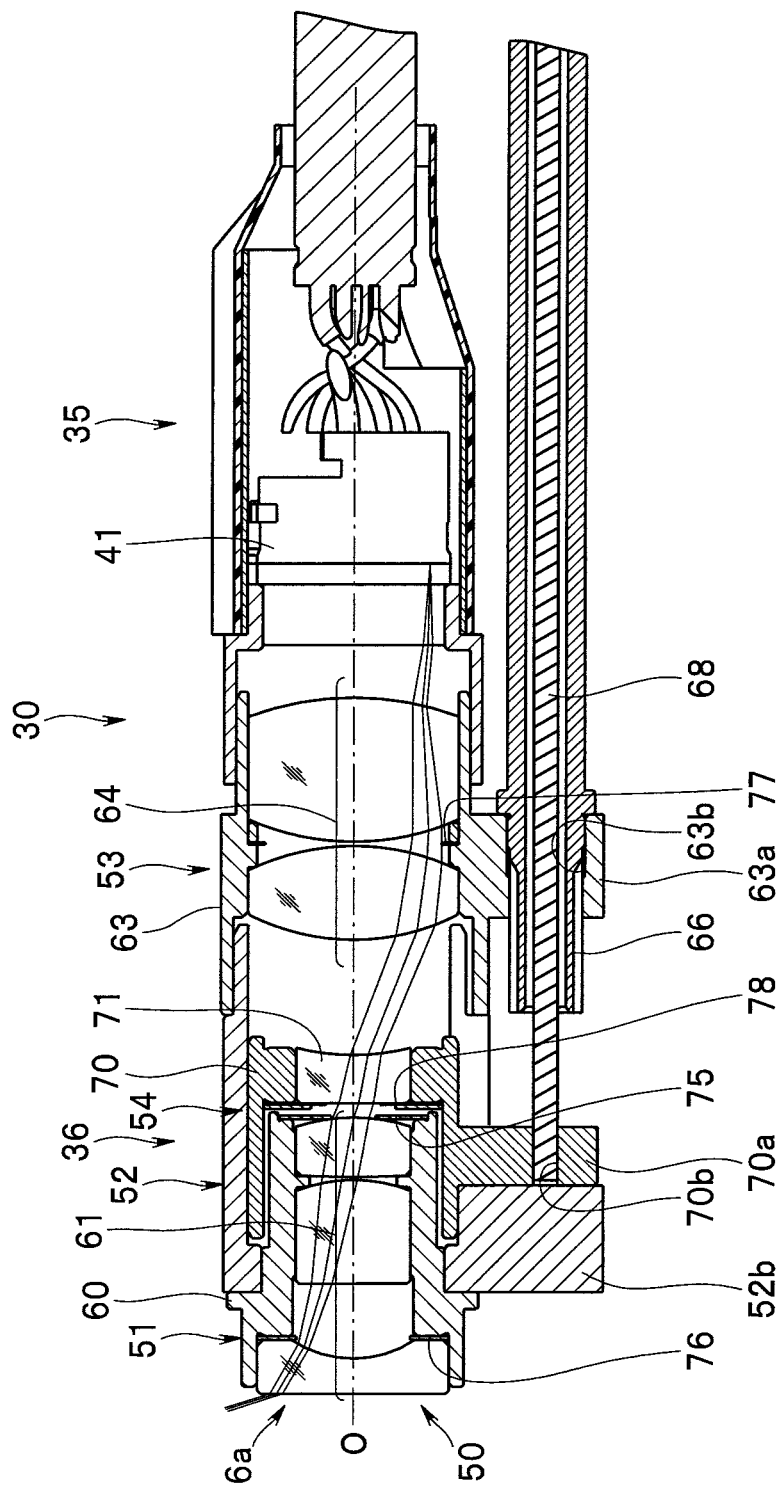
FIG. 7 is an explanatory diagram illustrating a behavior of light when an observation optical system is in a wide state.
Figure 8:
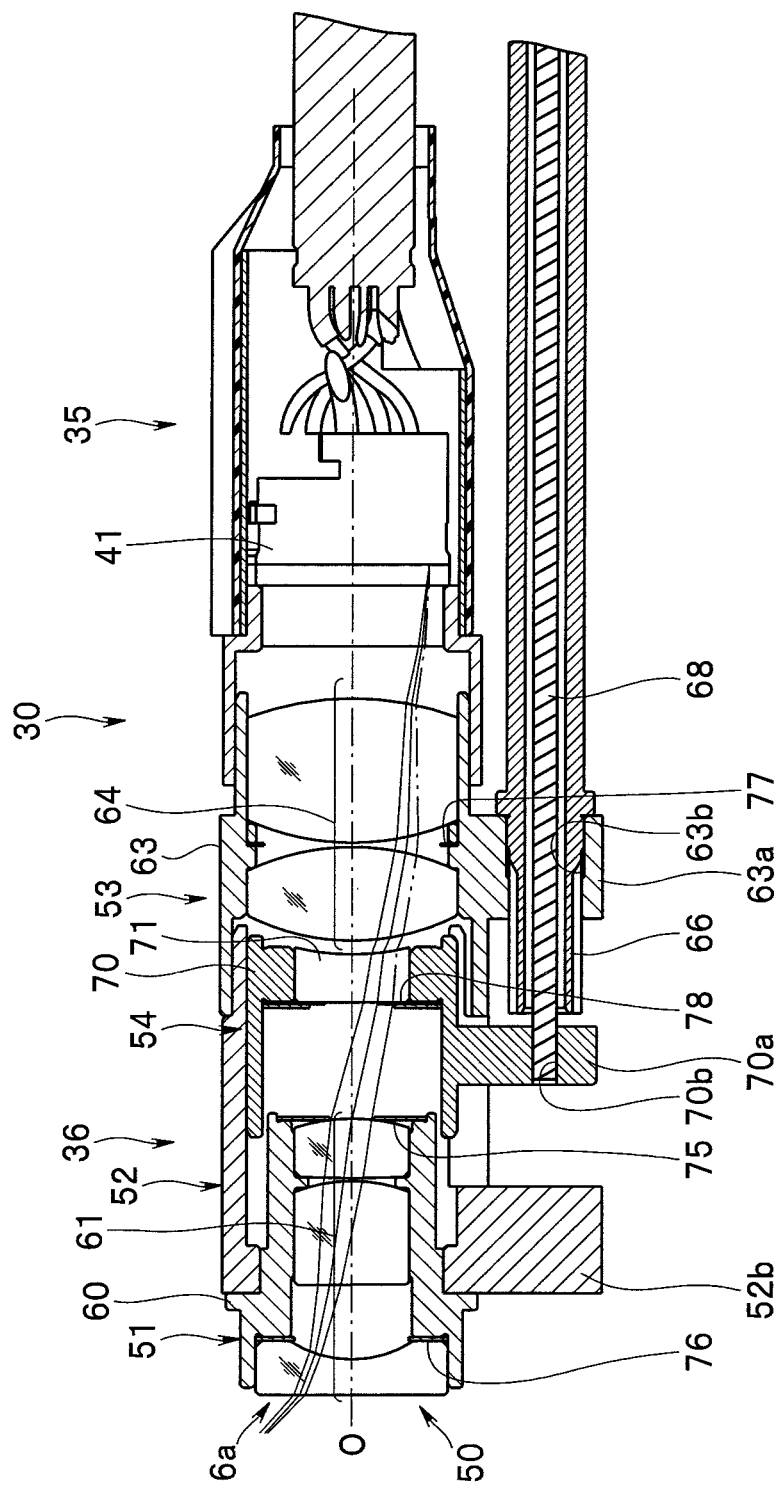
FIG. 8 is an explanatory diagram illustrating a behavior of light when the observation optical system is in a telephoto state.
Figure 9:
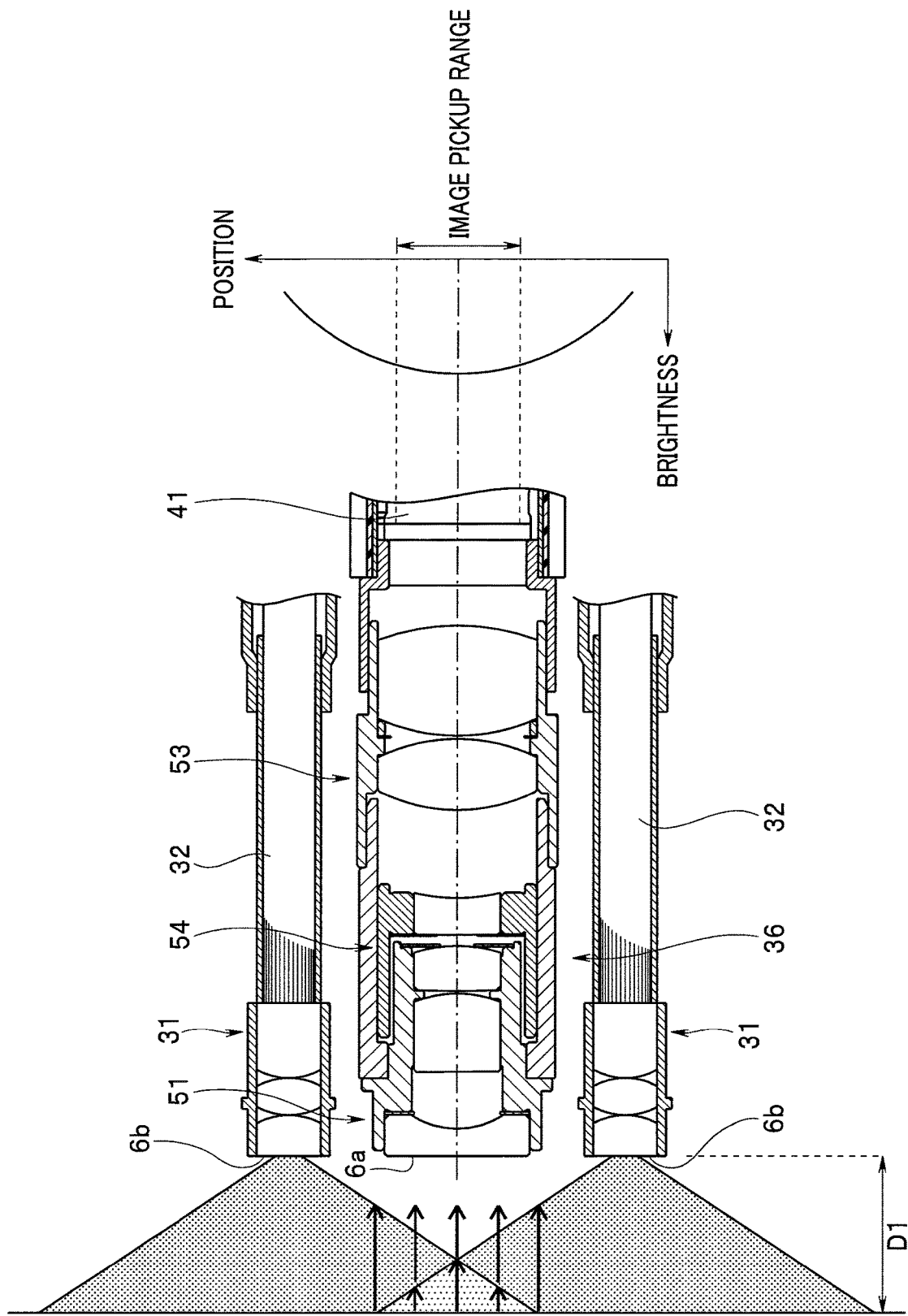
FIG. 9 is an explanatory diagram illustrating a brightness distribution on an image pickup surface when the observation optical system is in a wide state.
Figure 10:
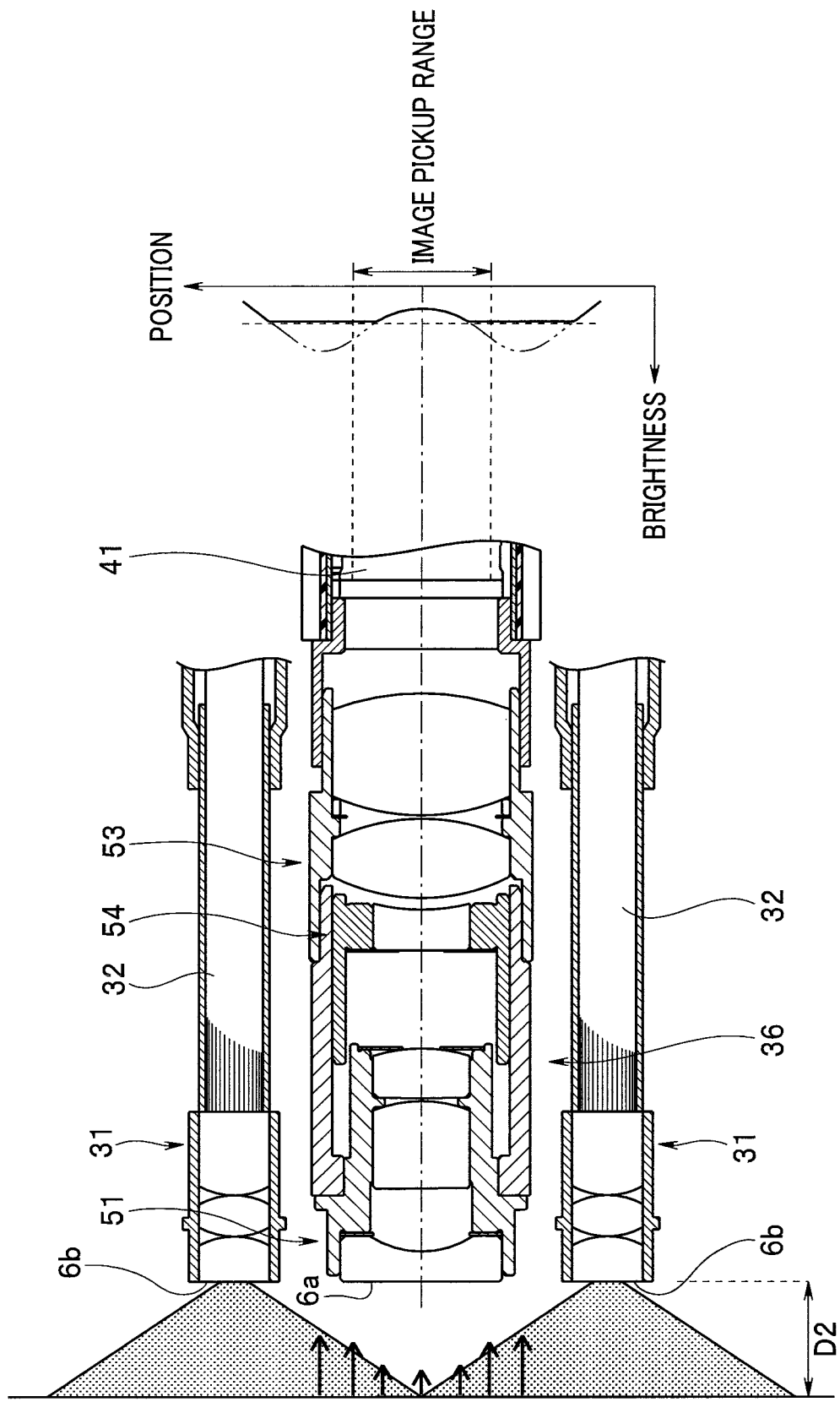
FIG. 10 is an explanatory diagram illustrating a brightness distribution on the image pickup surface when the observation optical system is in a telephoto state.
Figure 11:
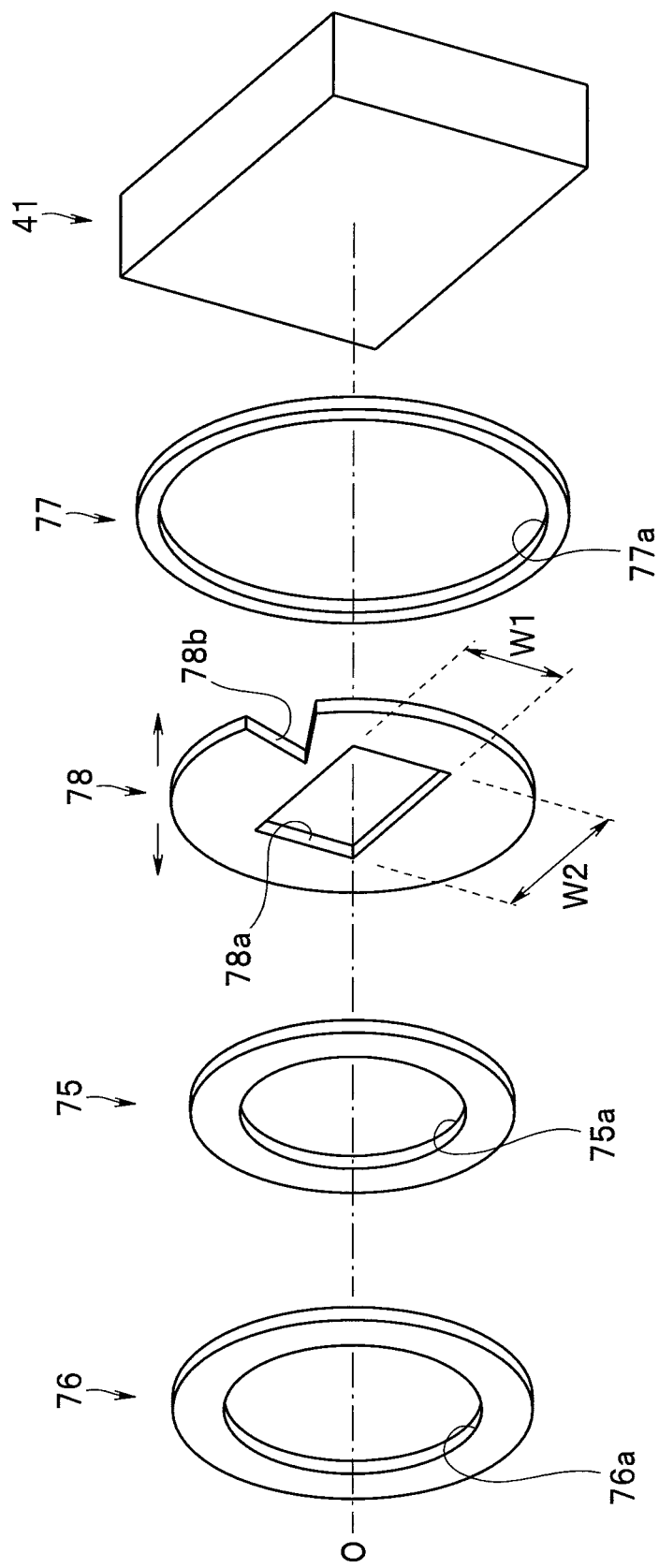
FIG. 11 is an explanatory diagram illustrating a relationship between each aperture and a solid-state image pickup device.
Figure 12:
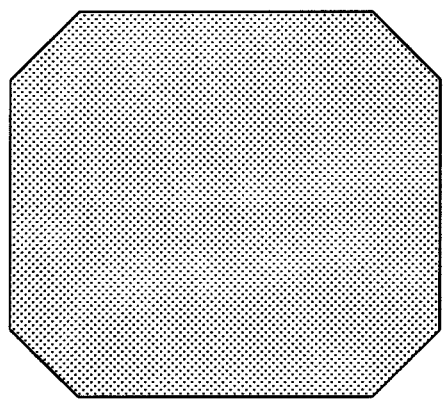
FIG. 12 is an explanatory diagram schematically illustrating a brightness distribution of an image when the observation optical system is in a telephoto state.
Figure 13:
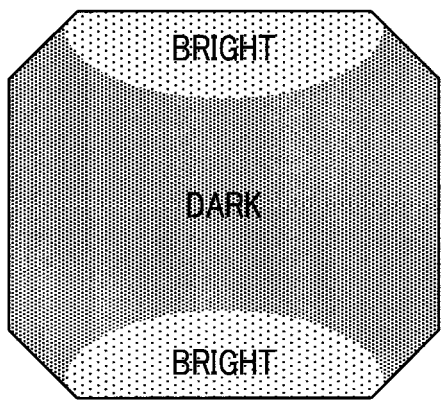
FIG. 13 is an explanatory diagram schematically illustrating a brightness distribution of an image when an observation optical system in which a movable lens frame does not include a brightness aperture is in a telephoto state as a comparative example.

An embodiment of the present invention will be described below with reference to the drawings. The drawings relate to an embodiment of the present invention, where FIG. 1 is an explanatory diagram illustrating an entire configuration of an endoscope, FIG. 2 is an end view of a distal end section, FIG. 3 is a cross-sectional view illustrating a distal end rigid member along a line III-III illustrated in FIG. 2, FIG. 4 is a cross-sectional view taken along a line IV-IV illustrated in FIG. 3, FIG. 5 is an exploded perspective view illustrating a movable lens frame, a brightness aperture, and a light shielding mask, FIG. 6 is a plan view of the brightness aperture disposed in the movable lens frame, FIG. 7 is an explanatory diagram illustrating a behavior of light when an observation optical system is in a wide state, FIG. 8 is an explanatory diagram illustrating a behavior of light when the observation optical system is in a telephoto state, FIG. 9 is an explanatory diagram illustrating a brightness distribution on an image pickup surface when the observation optical system is in a wide state, FIG. 10 is an explanatory diagram illustrating a brightness distribution on the image pickup surface when the observation optical system is in a telephoto state, FIG. 11 is an explanatory diagram illustrating a relationship between each aperture and a solid-state image pickup device, FIG. 12 is an explanatory diagram schematically illustrating a brightness distribution of an image when the observation optical system is in a telephoto state, and FIG. 13 is an explanatory diagram schematically illustrating a brightness distribution of an image when an observation optical system in which a movable lens frame does not include a brightness aperture is in a telephoto state as a comparative example.

Figure 1:
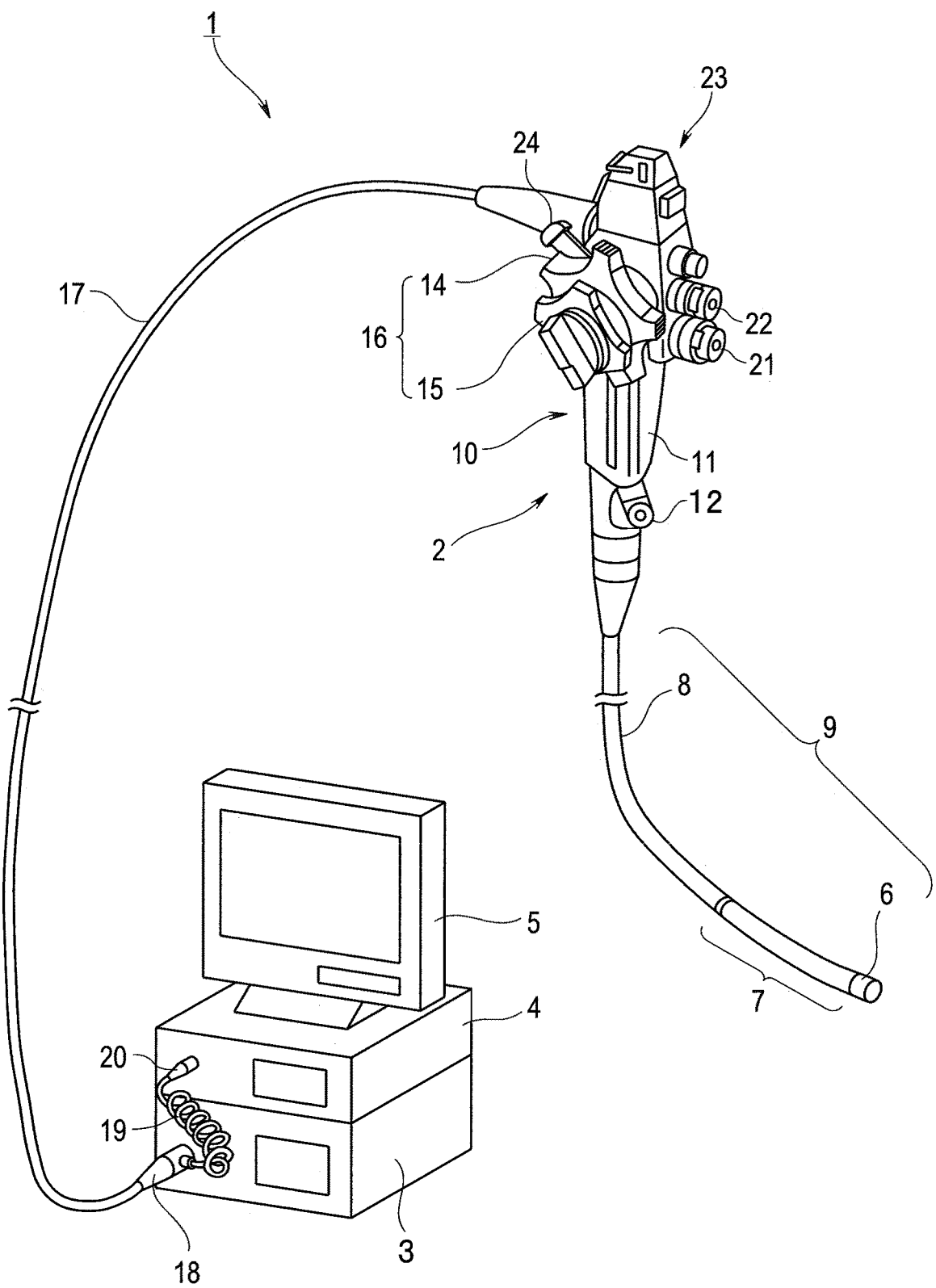
FIG. 1 is an explanatory diagram illustrating an entire configuration of an endoscope.

As illustrated in FIG. 1, an electronic endoscope system (hereinafter merely referred to as an endoscope system) 1 according to the present embodiment is configured such that an electronic endoscope apparatus as an endoscope (hereinafter merely referred to as an endoscope) 2, a light source apparatus 3, a video processor 4, and a color monitor 5 are electrically connected to one another.

The endoscope 2 includes an insertion section 9 and an operation section 10 from which the insertion section 9 is provided to extend, and a universal cord 17 extending from the operation section 10 is connected to the light source apparatus 3 via a scope connector 18.

A coil-shaped scope cable 19 is provided to extend from the scope connector 18. An electrical connector section 20 is provided on the other end side of the scope cable 19, and the electrical connector section 20 is connected to the video processor 4.

The insertion section 9 is configured such that a distal end section 6, a bending section 7, and a flexible tube section 8 are consecutively provided in this order from a distal end side.

As illustrated in FIG. 2, an observation window 6a, a plurality of (e.g., two) illumination windows 6b, a suction opening section 6c also serving as a treatment instrument introduction port, an observation window cleaning nozzle 6d, and a forward water feeding port 6e are disposed on a distal end surface of the distal end section 6.

In the present embodiment, the observation window 6a is arranged on the right side of the suction opening section 6c, for example. The two illumination windows 6b are vertically arranged with the observation window 6a sandwiched between the illumination windows, for example. Note that up-down and left-right directions in the present embodiment are defined to correspond to up-down and left-right directions of an endoscope image to be observed through the observation window 6a, for example.

The operation section 10 is provided with an operation section main body 11 constituting a grasping section, a forceps port 12 disposed on a distal end side of the operation section main body 11, a bending operation section 16 including two bending operation knobs 14 and 15 provided on a proximal end side of the operation section main body 11, an air/water feeding control section 21, a suction control section 22, a switch section 23 including a plurality of switches and configured to mainly operate an image pickup function, and an operation lever 24 configured to operate a movable lens provided within an image pickup unit, described below, to advance or retreat to operate a focusing function or a zooming function for adjusting a magnification on a wide/telephoto side or the like.

Next, a detailed configuration of the distal end section 6 in the endoscope 2 will be mainly described with reference to FIGS. 2 to 4.

As illustrated in FIGS. 3 and 4, the distal end section 6 includes a distal end rigid member 25 having a substantially cylindrical shape in an inner part. As illustrated in FIG. 3, a distal end cover 26 forming a distal end surface of the distal end section 6 is bonded and fixed to a distal end side of the distal end rigid member 25.

A plurality of bending pieces 28 constituting the bending section 7 are consecutively provided via a distal end frame 27 on a proximal end side of the distal end rigid member 25. Respective outer peripheries of the distal end rigid member 25, the distal end frame 27, and the bending pieces 28 are integrally coated with an outer covering 29. Further, an outer peripheral portion at a distal end of the outer covering 29 is fixed to the distal end rigid member 25 by a bobbin bonding section 29a.

As illustrated in FIGS. 3 and 4, the distal end rigid member 25 is provided with an image pickup unit holding hole 25a at a position corresponding to the observation window 6a. An image pickup unit 30 is arranged to be fitted and inserted into the image pickup unit holding hole 25a, and is fixed to the image pickup unit holding hole 25a by a set screw not illustrated. A distal end of the image pickup unit 30 is exposed to the outside of the distal end cover 26, whereby the observation window 6a is formed in the distal end section 6.

The distal end rigid member 25 is provided with an illumination unit holding hole 25b at a position corresponding to each of the illumination windows 6b. An illumination unit 31 is arranged to be fitted and inserted into the illumination unit holding hole 25b. A distal end of an illumination optical system 31a provided in the illumination unit 31 is exposed to the outside of the distal end cover 26, whereby the illumination window 6b is formed in the distal end section 6.

The illumination unit 31 in the present embodiment irradiates a subject using light to be supplied from the light source apparatus 3 via a light guide bundle 32 as a light source. Accordingly, a distal end side of the light guide bundle 32 is held in the illumination unit holding hole 25b on a proximal end side of the illumination unit 31. When a proximal end side of the light guide bundle 32 is inserted into the universal cord 17 from the insertion section 9 via the operation section 10, and the scope connector 18 is connected to the light source apparatus 3, illumination light from the light source apparatus 3 can be transmitted to the illumination window 6b.

The distal end rigid member 25 is provided with a through hole 25c configured to form the suction opening section 6c in the distal end section 6. The forceps port 12 in the operation section 10 communicates with the through hole 25c mainly via a treatment instrument channel 12a arranged to be inserted into the insertion section 9.

Further, the distal end rigid member 25 is provided with through holes 25d and 25e configured to respectively form the observation window cleaning nozzle 6d and the forward water feeding port 6e in the distal end section 6. Two cleaning tubes not illustrated to be inserted from the distal end section 6 to the universal cord 17 respectively communicate with the through holes 25d and 25e. The cleaning tubes are connected to a cleaning tank storing cleaning water and a compressor (both are not illustrated) on the side of the light source apparatus 3.

Next, a detailed configuration of the image pickup unit 30 will be described with reference to FIGS. 2, 5, and 6, for example.

As illustrated in FIG. 3, the image pickup unit 30 in the present embodiment is configured to include a solid-state image pickup unit 35 and an observation optical system unit 36 consecutively provided on a distal end side of the solid-state image pickup unit 35.

The solid-state image pickup unit 35 includes a solid-state image pickup device holding frame 40, and a front surface side of a solid-state image pickup device 41 as an image pickup device composed of a CCD, a CMOS, or the like is held in the solid-state image pickup device holding frame 40 via an optical member 42 such as a cover glass. A plurality of communication lines branched from a cable 43 are electrically connected to the solid-state image pickup device 41 via an FPC not illustrated or the like. The cable 43 is arranged to be inserted into the endoscope 2, and is electrically connected to the video processor 4 via the electrical connector section 20.

A reinforcement frame 44 is consecutively provided in an outer peripheral portion on a proximal end side of the solid-state image pickup device holding frame 40, and a thermal contraction tube 45 configured to coat the cable 43 up to a distal end section is provided on an outer periphery of the reinforcement frame 44.

The observation optical system unit 36 in the present embodiment is configured to include an observation optical system 50 of a focus switching type for implementing a focusing function or a zooming function by moving an internal lens to advance and retreat to change an optical characteristic (focal length).

More specifically, the observation optical system unit 36 is configured to include a front group lens unit 51 positioned on a distal end side, a connection frame 52 consecutively provided on a proximal end side of the front group lens unit 51, a rear group lens unit 53 connected to the front group lens unit 51 via the connection frame 52, and a movable lens unit 54 configured to be movable to advance and retreat along a shooting optical axis O direction within the connection frame 52.

The front group lens unit 51 is configured to include a front group lens frame 60 as a fixed frame and a front group lens 61 including a plurality of fixed lenses held in the front group lens frame 60.

The connection frame 52 is composed of a member having a substantially cylindrical shape. The connection frame 52 is provided with a slit 52a extending in the same direction as a direction along the shooting optical axis O. A proximal end side of the slit 52a is opened at a proximal end of the connection frame 52. On the other hand, a front-side stopper section 52b protruding along an outer diameter direction of the connection frame 52 is provided on a distal end side of the connection frame 52, and a distal end side of the slit 52a is closed by the front-side stopper section 52b.

The rear group lens unit 53 is configured to include a rear group lens frame 63 as a fixed frame having a distal end side connected to the front group lens frame 60 via the connection frame 52 and a rear group lens 64 including a plurality of fixed lenses held in the rear group lens frame 63.

The rear group lens frame 63 is provided with a wire supporting section 63a protruding along an outer diameter direction of the rear group lens frame 63. The wire supporting section 63a is positioned to oppose the front-side stopper section 52b when the rear group lens frame 63 is connected to the front group lens frame 60 via the connection frame 52. The wire supporting section 63a has a screw hole 63b penetrating through the wire supporting section along the optical axis O direction.

A rear-side stopper section 66 having a hollow male screw shape is screwed into the screw hole 63b. The rear-side stopper section 66 can adjust an amount of protrusion toward the front-side stopper section 52*b* depending on an amount of screwing into the screw hole 63*b*.

A wire guide 67 is consecutively provided on a proximal end side of the rear-side stopper section 66. An operation wire 68 configured to move to advance and retreat in conjunction with the operation lever 24 is inserted into the wire guide 67, and a distal end side of the operation wire 68 protrudes from the rear-side stopper section 66.

The movable lens unit 54 is configured to include a movable lens frame 70 as a moving frame configured to be movable within the connection frame 52 and a movable lens 71 held in the movable lens frame 70.

The movable lens frame 70 is provided with an operation rod 70*a* protruding along an outer diameter direction of the movable lens frame 70. The operation rod 70*a* protrudes to the outside of the connection frame 52 via the slit 52*a*, and opposes the front-side stopper section 52*b* and the rear-side stopper section 66. The operation rod 70*a* has a wire holding hole 70*b* penetrating through the operation rod along the shooting optical axis O direction, and a distal end of the operation wire 68 protruding from the rear-side stopper section 66 is held in the wire holding hole 70*b*.

As a result, the movable lens unit 54 can move to advance and retreat along the shooting optical axis O between a wide position where the operation rod 70*a* abuts on the front-side stopper section 52*b* and a telephoto position where the operation rod 70*a* abuts on the rear-side stopper section 66, for example, in conjunction with an operation for the operation lever 24. Note that the wide position and the telephoto position of the movable lens unit 54 are determined by a characteristic, a layout, or the like of each of the optical members (the front group lens 61, the rear group lens 64, and the movable lens 71) constituting the observation optical system unit 36, and a position where the operation rod 70*a* abuts on the front-side stopper section 52*b* and a position where the operation rod 70*a* abuts on the rear-side stopper section 66 may be respectively set as a telephoto position and a wide position.

In the observation optical system unit 36 having such a configuration, the front group lens frame 60 is provided with a brightness aperture 75 configured to determine a brightness of the observation optical system 50 by imposing a predetermined restriction on incident light and a first flare aperture 76 configured to block stray light or the like.

In the present embodiment, the brightness aperture 75 is provided on a proximal end side of the front group lens 61, for example. The brightness aperture 75 includes an opening section 75*a* as a first opening section having a circular shape centered around the shooting optical axis O (see FIG. 11), and can uniformly cut (restrict) a part of light incident on the front group lens 61 with the shooting optical axis O as a center.

The first flare aperture 76 is provided on a distal end side of the front group lens 61, for example. The first flare aperture 76 includes a circular opening section 76*a* centered around the shooting optical axis O, and can block stray light or the like to be incident on the front group lens 61.

The rear group lens frame 63 is provided with a second flare aperture 77 configured to block stray light or the like.

The second flare aperture 77 is provided in the middle of the rear group lens 64, for example. The second flare aperture 77 includes a circular opening section 77*a* centered around the shooting optical axis O, and can block stray light or the like incident on the rear group lens 64 via the front group lens 61 and the movable lens 71.

The movable lens frame 70 is provided with a light shielding aperture 78 configured to impose a predetermined restriction on incident light.

The light shielding aperture 78 is provided on a distal end side of the movable lens 71, for example. The light shielding aperture 78 is an aperture configured to reduce a brightness on the side of the illumination unit 31 together provided in the image pickup unit 30 (the observation optical system unit 36) when the movable lens unit 54 has moved toward the telephoto side. Accordingly, the light shielding aperture 78 includes an opening section 78*a* as a second opening section in which a shape of the light shielding aperture 78 in a direction perpendicular to the shooting optical axis O is an irregular shape corresponding to an arrangement of the illumination unit 31.

More specifically, an opening shape of the opening section 78*a* is set based on an experiment, a simulation, or the like, and the opening section 78*a* in the present embodiment is a rectangular opening section in which an opening width W1 in an up-down direction is narrower than an opening width W2 in a left-right direction to correspond to an arrangement in which the two illumination units 31 are together provided above and below the image pickup unit 30, as illustrated in FIGS. 5, 6, and 11, for example. In other words, the opening section 78*a* in the present embodiment is an opening section, which is rectangular in shape in a planar view, having long sides in the up-down direction corresponding to respective arrangements of the illumination units 31 and having short sides in the left-right direction in which the illumination units 31 are not arranged. Further, as illustrated in FIG. 11, an extension direction of each of the sides (the pair of long sides and the pair of short sides) of the opening section 78*a* in the present embodiment is set to match an extension direction of each of the sides of the solid-state image pickup device 41.

In this case, to position the light shielding aperture 78 in which the opening section 78*a* has an irregular shape with respect to the shooting optical axis O relative to the movable lens frame 70 with high accuracy, an index for positioning 78*b* is provided in an edge side portion of the light shielding aperture 78.

The index 78*b* is composed of a notch portion set to have one side arranged on an extension line 1 of a side surface of the operation rod 70*a* provided in the movable lens frame 70, as illustrated in FIG. 6, for example.

Note that to prevent light from leaking out of the index 78*b*, a light shielding mask 79 including an opening section 79*a* larger than the opening section 78*a* and capable of covering the index 78*b* is arranged to overlap the brightness aperture 78, as illustrated in FIG. 5, for example.

Thus, the light shielding aperture 78 held in the movable lens frame 70 is moved to advance and retreat along the shooting optical axis O direction integrally with the movable lens frame 70.

When the movable lens frame 70 is advanced toward a distal end side along the shooting optical axis O direction, and is at a wide position defined by the front-side stopper section 52*b*, as illustrated in FIG. 7, the light shielding aperture 78 makes light that has passed through the brightness aperture 75 incident on the movable lens 71 without cutting the light.

As a result, in observation performed when the movable lens unit 54 is at the wide position, as illustrated in FIG. 9, light having a substantially uniform brightness is formed on an image pickup surface of the solid-state image pickup device 41 over an entire area of an image pickup range. Thus, a luminance difference of a picked-up image can be suppressed.

In other words, at the time of wide observation performed when the movable lens unit 54 is at an advance position within the observation optical system unit 36, the observation window 6a and the illumination window 6b are respectively arranged at positions sufficiently spaced apart (e.g., positions a predetermined distance D1 away) from a subject (object). Therefore, illumination light irradiated from each of the illumination units 31 is sufficiently diffused, and an observation region on the subject is irradiated with substantially uniform illumination light. Reflected light of the illumination light thus uniformly irradiated is incident on the observation optical system unit 36. A part of light thus incident on the observation optical system unit 36 is equally cut in all directions centered around the shooting optical axis O by the brightness aperture 75. Light that has passed through the brightness aperture 75 is formed on the solid-state image pickup device 41 without being cut by the light shielding aperture 78. As a result, the luminance difference of the picked-up image is suppressed.

On the other hand, when the movable lens frame 70 retreats toward a proximal end side along the shooting optical axis O direction, and is at a telephoto position defined by the rear-side stopper section 66, as illustrated in FIG. 8, the light shielding aperture 78 can make predetermined light fluxes, which have passed through the brightness aperture 75, incident on the movable lens 71 after cutting some of the light fluxes.

As a result, in observation performed when the movable lens unit 54 is at the telephoto position, as illustrated in FIG. 10, light having a substantially uniform brightness is formed on the image pickup surface of the solid-state image pickup device 41 over the entire area of the image pickup range. Thus, the luminance difference of the picked-up image can be suppressed.

In other words, at the time of telephoto observation performed when the movable lens unit 54 is at a retreat position within the observation optical system unit 36, the observation window 6a and the illumination windows 6b are respectively arranged at positions significantly close (e.g., positions as close as a predetermined distance D2 (<<D1)) to a subject (object). Therefore, illumination light irradiated from each of the illumination units 31 is not sufficiently diffused, but an observation region on the subject is irradiated with non-uniform illumination light that is bright only in the vicinity of each of the illumination units 31. Reflected light of the illumination light thus non-uniformly irradiated is incident on the observation optical system unit 36. A part of light thus incident on the observation optical system unit 36 is equally cut in all directions centered around the shooting optical axis O by the brightness aperture 75. A part of light that has passed through the brightness aperture 75 is formed on the solid-state image pickup device 41 after light in a specific direction corresponding to the illumination unit 31 is cut by the light shielding aperture 78. As a result, the luminance difference of the picked-up image is suppressed.

In other words, if the light shielding aperture 78 is not provided, a brightness (light amount) of light formed on the image pickup surface becomes non-uniform, as indicated by a two-dot and dash line in a brightness characteristic in FIG. 10, and unevenness in brightness also occurs on the picked-up image, as illustrated in FIG. 13. On the other hand, when the light shielding aperture 78 cuts a part of light on the side of each of the illumination units 31 (reduces light), a brightness (light amount) of light formed on the image pickup surface becomes substantially uniform, as indicated by a solid line in the brightness characteristic in FIG. 10, and the unevenness in brightness on the picked-up image is suppressed, as illustrated in FIG. 12. Note that even when the light shielding aperture 78 thus further cuts a part of incident light, a picked-up image having an appropriate brightness can be obtained by feedback control of the light amount in the light source apparatus 3, for example.

According to the embodiment, when the image pickup unit 30 includes the brightness aperture 75 held in the front group lens frame 60 and the light shielding aperture 78 held in the movable lens frame 70, the opening section 78a formed in the light shielding aperture 78 has an opening shape different from an opening shape of the opening section 75a formed in the brightness aperture 75, and the light shielding aperture 78 is configured to block predetermined light fluxes that have passed through the brightness aperture 75 only when the movable lens frame 70 is on the telephoto side, the luminance difference of the picked-up image can also be suppressed when image pickup is performed at a position brought close to the subject.

In this case, more specifically, when the opening section 78a in the light shielding aperture 78 is set such that an opening width W1 in a direction in which the illumination unit 31 (the illumination optical system 31a) is arranged becomes smaller than an opening width W2 in a direction other than a direction in which the illumination unit 31 (the illumination optical system 31a) is arranged, the luminance difference of the picked-up image on the telephoto side can be accurately suppressed.

In other words, when the opening section 78a has a rectangular shape in which the long sides are arranged in the up-down direction in which the pair of illumination units 31 is arranged as viewed from the shooting optical axis O and the short sides are arranged in the left-right direction in which the illumination units 31 are not arranged, and the light shielding aperture 78 cuts some of light fluxes on the upper side and the lower side among light fluxes to be incident on the movable lens 71 when the movable lens unit 54 is on the telephoto side, the luminance difference of the picked-up image can also be suppressed when image pickup is performed at a position brought close to the subject.

As a configuration of the index for positioning the above-described light shielding aperture 78 in the movable lens frame 70, various changes can be made.

Figure 14:
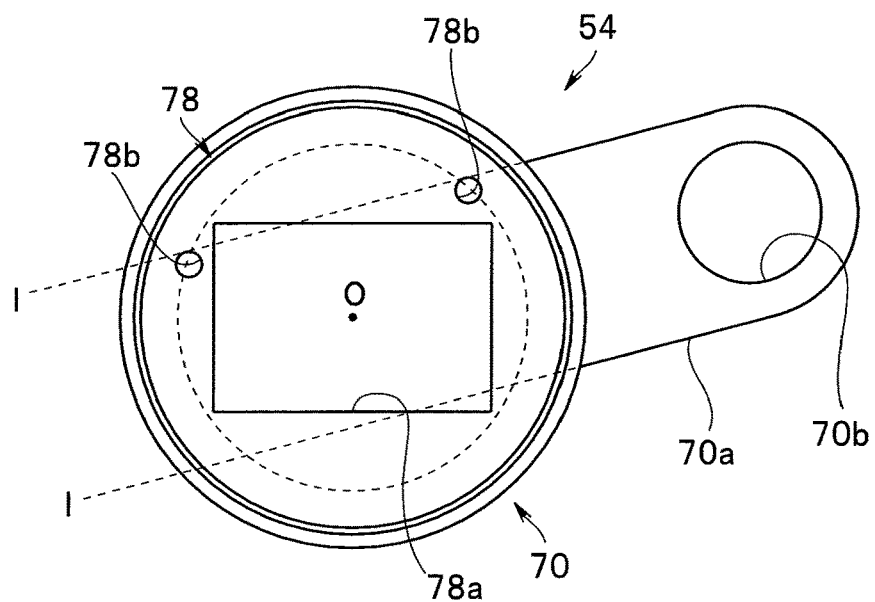
FIG. 14 is a plan view of a brightness aperture disposed in a movable lens frame according to a first modification.

For example, as illustrated in FIG. 14, an index 78b can also be constituted by a pair of circular holes contacting an extension line 1 on a side surface of an operation rod 70a.

Figure 15:
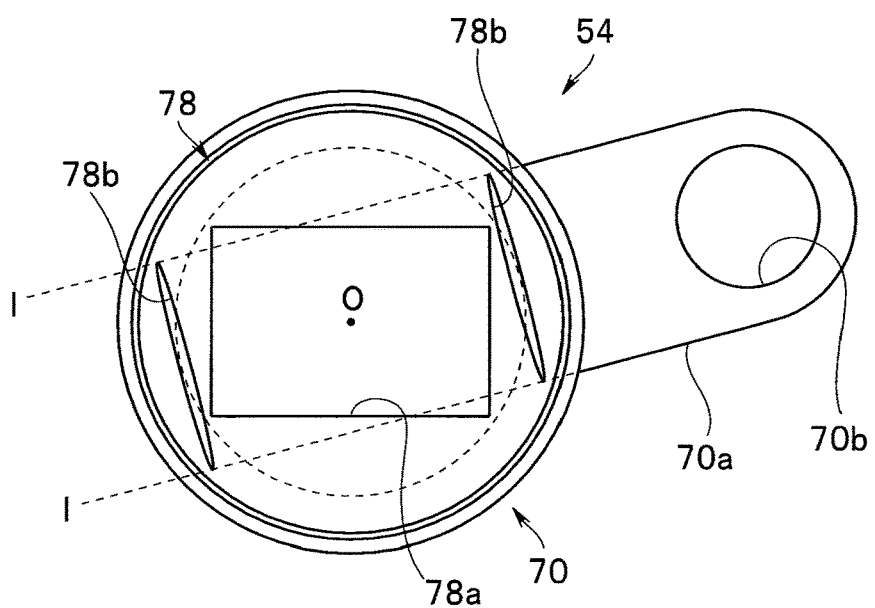
FIG. 15 is a plan view of a brightness aperture disposed in a movable lens frame according to a second modification.

For example, as illustrated in FIG. 15, an index 78b can also be constituted by a pair of long holes contacting an extension line 1 on a side surface of an operation rod 70a.

Figure 16:
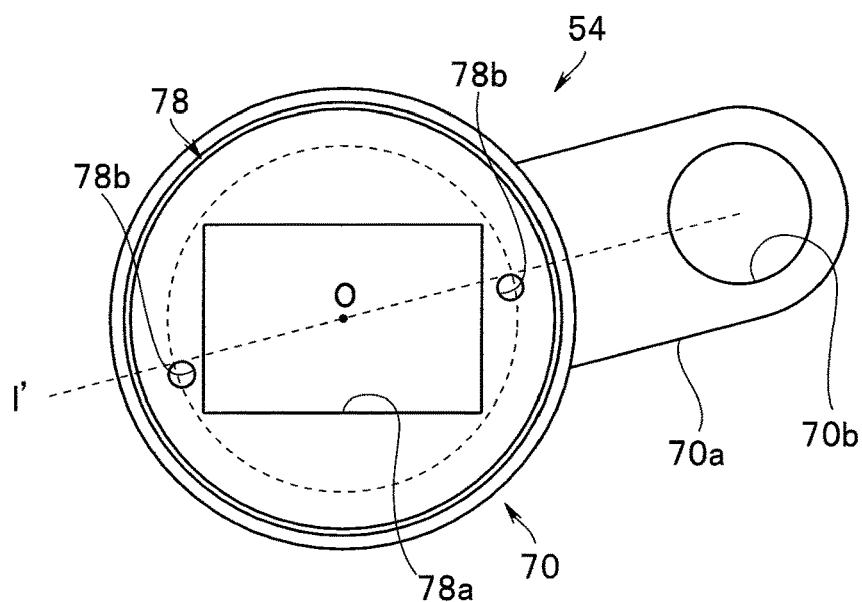
FIG. 16 is a plan view of a brightness aperture disposed in a movable lens frame according to a third modification.

For example, as illustrated in FIG. 16, an index 78b can also be constituted by a pair of circular holes passing through a center of the wire holding hole 70b and contacting a line l' parallel to an extension line 1 on a side surface of an operation rod 70a.

Figure 17:
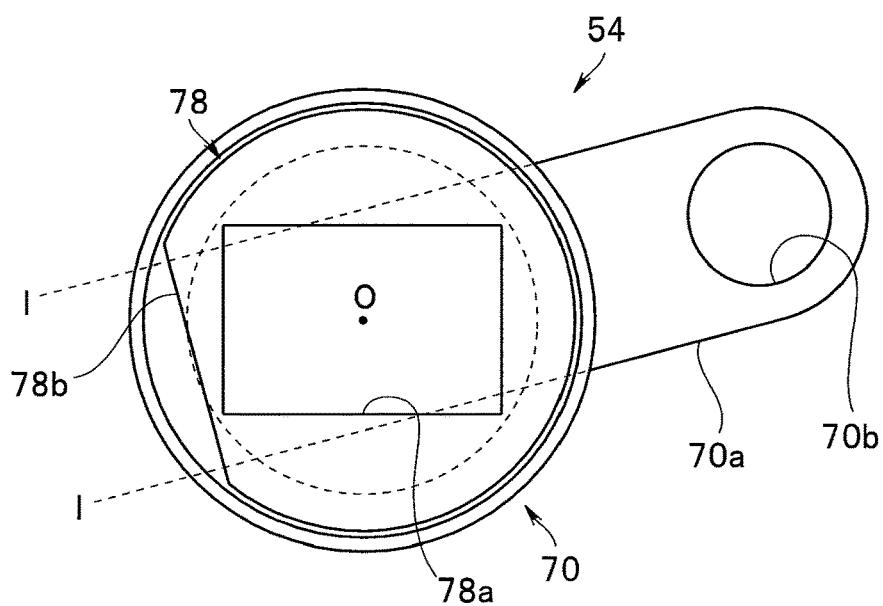
FIG. 17 is a plan view of a brightness aperture disposed in a movable lens frame according to a fourth modification.

For example, as illustrated in FIG. 17, an index 78b can also be constituted by a notch perpendicular to an extension line 1 on a side surface of an operation rod 70a.

Figure 18:
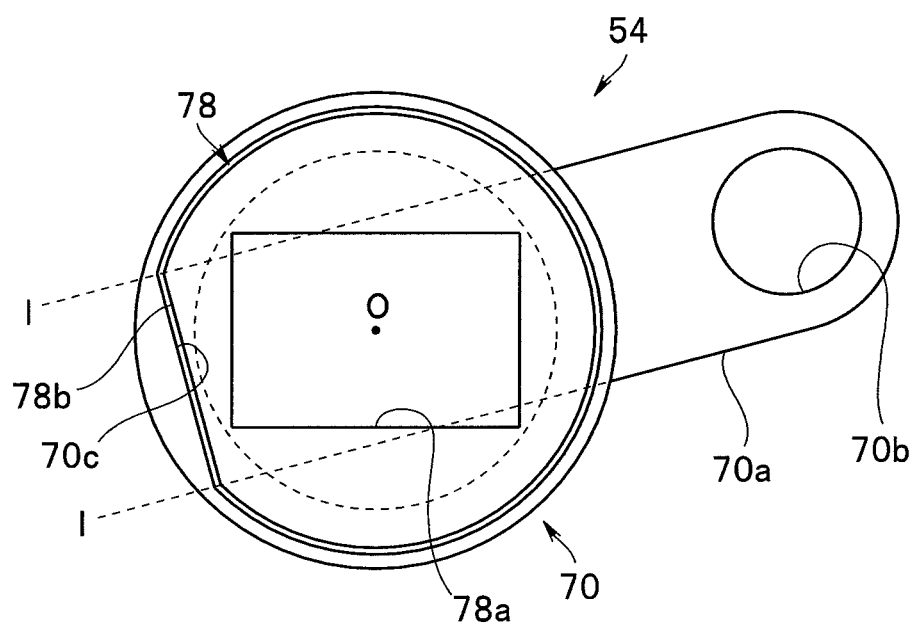
FIG. 18 is a plan view of a brightness aperture disposed in a movable lens frame according to a fifth modification.

Further, for example, as illustrated in FIG. 18. a step section 70c engaging with an index 78b perpendicular to an extension line 1 can also be provided in a movable lens frame 70.

Figure 19:
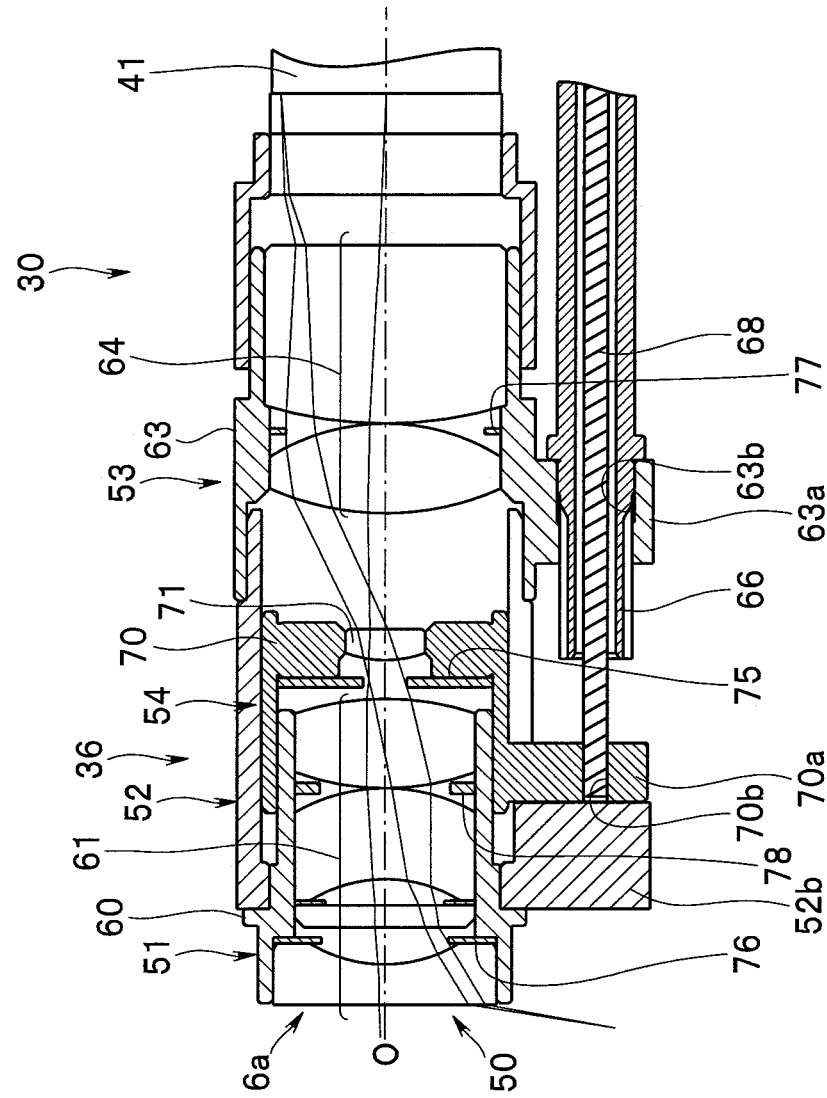
FIG. 19 is an explanatory diagram illustrating a behavior of light when an observation optical system is in a wide state according to a sixth modification.
Figure 20:
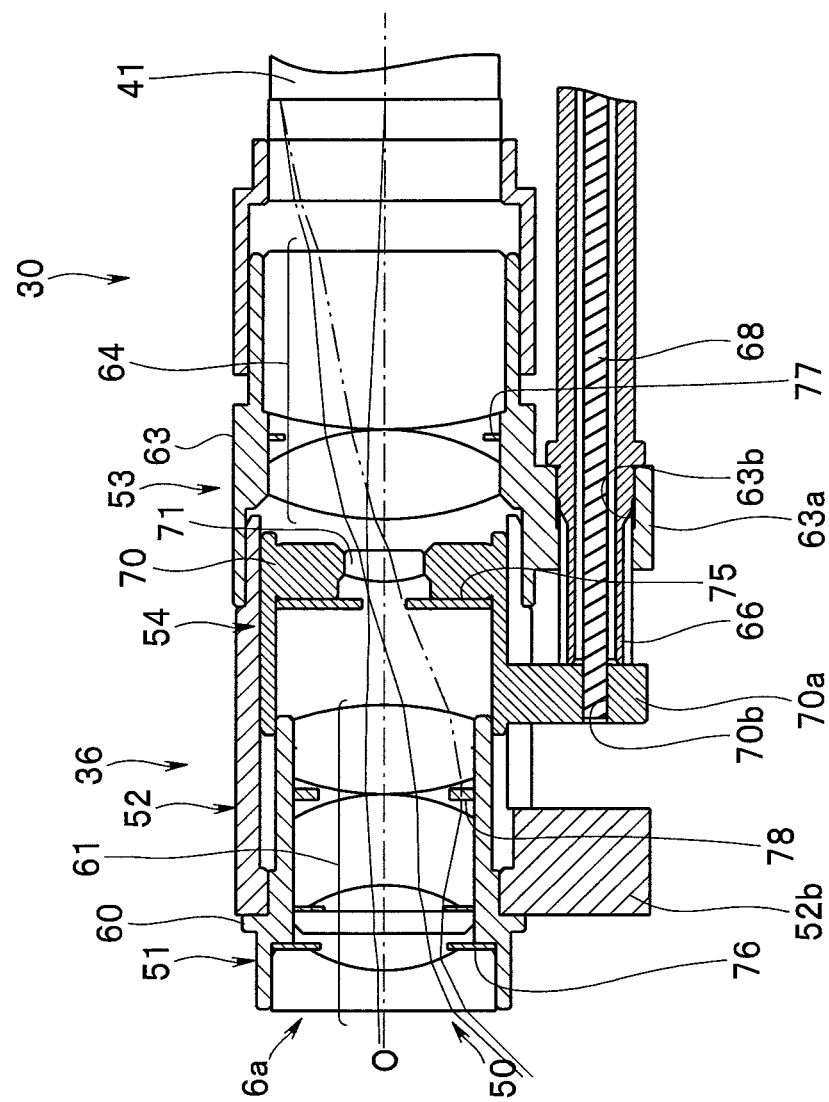
FIG. 20 is an explanatory diagram illustrating a behavior of light when the observation optical system is in a telephoto state according to the sixth modification.

An arrangement of the light shielding aperture 78 is not limited to the above-described arrangements, but a light shielding aperture 78 can also be provided in a fixed frame (e.g., a front group lens frame 60) depending on an optical characteristic of an observation optical system 50 in an observation optical system unit 36 and an arrangement of a brightness aperture 75, for example, as illustrated in FIGS. 19 and 20, for example.

In other words, in the observation optical system unit 36 illustrated in FIGS. 19 and 20, the brightness aperture 75 is provided in a movable lens frame 70 on a distal end side of a movable lens 71, for example.

The light shielding aperture 78 is provided in the front group lens frame 60 in the middle of a front group lens 61, for example.

Respective opening shapes of an opening section 75a in the brightness aperture 75 and an opening section 78a in the light shielding aperture 78 are set based on an experiment, a simulation, or the like. The opening section 75a in the present modification is set to have a circular shape centered around a shooting optical axis O. On the other hand, the opening section 78a in the present modification is a rectangular opening section in which an opening width W1 in an up-down direction is narrower than an opening width W2 in a left-right direction to correspond to an arrangement in which two illumination units 31 are together provided above and below an image pickup unit 30.

As illustrated in FIG. 19, the light shielding aperture 78 can pass all light fluxes that can pass through light shielding aperture 78 provided in the movable lens frame 70 when the movable lens frame 70 is moving toward a wide side.

On the other hand, as illustrated in FIG. 20, the light shielding aperture 78 can block some of predetermined light fluxes that can pass through the brightness aperture 75 provided in the movable lens frame 70 when the movable lens frame 70 is moving toward a telephoto side.

In the modifications, a similar function and effect to the function and effect in the above-described embodiment can also be obtained.

Note that the present invention is not limited to the above-described embodiment, but various modifications and changes can be made, and also fall within the technical scope of the present invention.

What is claimed is:

1. An endoscope comprising:
    an optical system including a fixed lens and a movable lens, the optical system being configured to switch a focal position to a subject at a first distance and a subject at a second distance closer than the first distance;
    a fixed frame configured to hold the fixed lens;
    a moving frame configured to hold the movable lens, the moving frame being movable toward a side corresponding to the first distance and a side corresponding to the second distance along a direction of an optical axis of the optical system to move the movable lens relative to the fixed lens;
    a brightness aperture configured to determine a brightness of the optical system;
    an image pickup sensor configured to generate a video signal from an object image formed by the optical system; and
    a light shielding aperture provided on the moving frame, the light shielding aperture being configured to change an amount of blocking some predetermined light fluxes that can pass through the brightness aperture when the moving frame moves from the side corresponding to the first distance to the side corresponding to the second distance.

2. The endoscope according to claim 1, wherein an opening in the light shielding aperture has an opening shape different from an opening in the brightness aperture.

3. The endoscope according to claim 2, wherein the opening in the light shielding aperture is set such that an opening width in a direction in which an illumination optical system together provided in a vicinity of the optical system is arranged is smaller than an opening width in a direction other than the direction in which the illumination optical system is arranged.

4. The endoscope according to claim 3, wherein the opening in the light shielding aperture is a rectangular opening having a pair of long sides and a pair of short sides.

5. The endoscope according to claim 4, wherein a direction in which the pair of long sides and the pair of short sides are arranged matches a direction of each of sides of the image pickup sensor.

6. The endoscope according to claim 1, wherein the light shielding aperture includes an index for performing positioning around the optical axis when held in the moving frame.

7. The endoscope according to claim 1, wherein the light shielding aperture is arranged in the fixed frame.

8. The endoscope according to claim 3, wherein, in the light shielding aperture, a distance from an edge forming an opening configured to pass light to the optical axis is longer in a direction in which the illumination optical system is not arranged than in a direction in which the illumination optical system is arranged using the optical axis as a reference.

9. The endoscope according to claim 1, wherein the light shielding aperture is configured to block some light fluxes that have passed through the brightness aperture.

10. An endoscope comprising:
    an illumination optical system configured to irradiate an object with light;
    an observation optical system including a fixed lens and a movable lens, the observation optical system being configured to switch a focal position to a first distance and a second distance closer than the first distance;
    a fixed frame configured to hold the fixed lens;
    a moving frame configured to hold the movable lens, the moving frame being configured to move the movable lens relative to the fixed lens so as to switch the focal position to the first distance and the second distance by moving the moving frame to advance and retreat along a direction of an optical axis of the optical system;
    an image pickup sensor configured to generate a video signal from an object image formed by the observation optical system;
    a brightness aperture configured to restrict incident light and determine a brightness of the observation optical system; and
    a light shielding aperture provided on the moving frame, the light shielding aperture being configured to restrict incident light and to change a light amount restricted according to a focal length changing from the first distance to the second distance, wherein
    in the light shielding aperture, a distance from an edge forming an opening configured to pass light to the optical axis is longer in a direction in which the illumination optical system is not arranged than in a direction in which the illumination optical system is arranged using the optical axis as a reference.

11. The endoscope according to claim 10, wherein the light shielding aperture includes an index for performing positioning around the optical axis when held in the moving frame.

12. The endoscope according to claim 11, wherein the light shielding aperture is arranged in the fixed frame.

13. The endoscope according to claim 10 wherein the light shielding aperture is configured to block some light fluxes that have passed through the brightness aperture.

14. An image pickup unit comprising:
- an optical system including a fixed lens and a movable lens, the optical system being configured to switch a focal position to a subject at a first distance and a subject at a second distance closer than the first distance;
- a fixed frame configured to hold the fixed lens;
- a moving frame configured to hold the movable lens, the moving frame being movable toward a side corresponding to the first distance and a side corresponding to the second distance along a direction of an optical axis of the optical system to move the movable lens relative to the fixed lens;
- a brightness aperture configured to determine a brightness of the optical system;
- an image pickup sensor configured to generate a video signal from an object image formed by the optical system; and
- a light shielding aperture provided on the moving frame, the light shielding aperture being configured to change an amount of blocking some predetermined light fluxes that can pass through the brightness aperture when the moving frame moves from the side corresponding to the first distance to the side corresponding to the second distance.

15. The image pickup unit according to claim 14, wherein an opening in the light shielding aperture has an opening shape different from an opening in the brightness aperture.

16. The image pickup unit according to claim 15, wherein the opening in the light shielding aperture is set such that an opening width in a direction in which an illumination optical system together provided in the vicinity of the optical system is smaller than an opening width in a direction other than the direction in which the illumination optical system is arranged.

17. The image pickup unit according to claim 16, wherein the opening in the light shielding aperture is a rectangular opening having a pair of long sides and a pair of short sides.

18. The image pickup unit according to claim 17, wherein a direction in which the pair of long sides and the pair of short sides are arranged matches a direction of each of sides of the image pickup sensor.

19. The image pickup unit according to claim 14, wherein the light shielding aperture includes an index for performing positioning around the optical axis when held in the moving frame.

20. The image pickup unit according to claim 14, wherein the light shielding aperture is arranged in the fixed frame.

21. The image pickup unit according to claim 14, wherein the light shielding aperture is configured to block some light fluxes that have passed through the brightness aperture.

* * * * *